(12) United States Patent
Zhang et al.

(10) Patent No.: US 8,709,079 B2
(45) Date of Patent: Apr. 29, 2014

(54) IOL WITH VARYING CORRECTION OF CHROMATIC ABERRATION

(75) Inventors: Xiaoxiao Zhang, Fort Worth, TX (US); Costin Eugene Curatu, Crowley, TX (US); Krishnakumar Venkateswaran, Burleson, TX (US); Daniel Robert Carson, Forth Worth, TX (US); Mutlu Karakelle, Fort Worth, TX (US); Xin Hong, Fort Worth, TX (US); Yueai Liu, Fort Worth, TX (US)

(73) Assignee: Novartis AG, Basel (CH)

( * ) Notice: Subject to any disclaimer, the term of this patent is extended or adjusted under 35 U.S.C. 154(b) by 41 days.

(21) Appl. No.: 12/780,381

(22) Filed: May 14, 2010

(65) Prior Publication Data

US 2010/0312337 A1  Dec. 9, 2010

Related U.S. Application Data

(60) Provisional application No. 61/185,510, filed on Jun. 9, 2009.

(51) Int. Cl.
*A61F 2/16* (2006.01)
*G02C 7/00* (2006.01)

(52) U.S. Cl.
USPC .................. 623/6.31; 623/6.3; 351/159.11

(58) Field of Classification Search
USPC ..................... 623/6.27–6.31, 6.24
See application file for complete search history.

(56) References Cited

U.S. PATENT DOCUMENTS

| 4,642,112 | A | * | 2/1987 | Freeman | .................. 623/6.3 |
| 4,655,565 | A | | 4/1987 | Freeman | |
| 5,117,306 | A | | 5/1992 | Cohen | |
| 5,257,132 | A | | 10/1993 | Ceglio et al. | |
| 5,470,932 | A | | 11/1995 | Jinkerson | |
| 5,543,504 | A | | 8/1996 | Jinkerson | |
| 5,699,142 | A | | 12/1997 | Lee et al. | |
| 7,441,894 | B2 | | 10/2008 | Zhang et al. | |

(Continued)

FOREIGN PATENT DOCUMENTS

| EP | 2045648 | 4/2009 |
| WO | WO 99/28769 | 6/1999 |
| WO | WO 2006/047698 | 5/2006 |

OTHER PUBLICATIONS

International Search Report for PCT/US2010/037371, 3 pages.

(Continued)

*Primary Examiner* — David H Willse
*Assistant Examiner* — Tiffany Shipmon
(74) *Attorney, Agent, or Firm* — Jonathan E. Prejean

(57) ABSTRACT

An ophthalmic lens includes an optical filter operable to filter out at least visible light having a wavelength less than 450 nm. The lens also includes a first diffractive structure adapted to produce a focus for visible light in a first wavelength range above 550 nm and to reduce longitudinal chromatic aberration to less than one diopter for incoming visible light in the first wavelength range. The lens also includes a second diffractive structure outside the first diffractive structure in a radial direction and adapted to produce a focus for visible light in a second wavelength range between 450 nm and 550 nm. The second diffractive structure is also adapted to reduce longitudinal chromatic aberration for incoming visible light in the second wavelength range to less than one diopter while allowing longitudinal chromatic aberration in the first wavelength range in an amount greater than the first diffractive structure.

15 Claims, 3 Drawing Sheets

(56) References Cited

U.S. PATENT DOCUMENTS

| | | | |
|---|---|---|---|
| 7,481,532 B2 | 1/2009 | Hong et al. | |
| 2004/0252274 A1* | 12/2004 | Morris et al. | 351/168 |
| 2006/0098162 A1* | 5/2006 | Bandhauer et al. | 351/159 |
| 2006/0098163 A1 | 5/2006 | Bandhauer et al. | |
| 2006/0212117 A1* | 9/2006 | Lang et al. | 623/6.23 |

OTHER PUBLICATIONS

Written Opinion of the International Searching Authority, International Application No. PCT/US2010/037371, Jun. 4, 2010, 12 pages.

International Search Report for PCT/US2010/037373, 2 pages.

Written Opinion of the International Searching Authority, International Application No. PCT/US2010/037373, 8 pages.

PCT International Preliminary Report on Patentability and Written Opinion of the International Searching Authority, International Application No. PCT/US2010/037371, Dec. 22, 2011, 14 pages.

PCT International Preliminary Report on Patentability and Written Opinion of the International Searching Authority, International Application No. PCT/US2010/037373, Dec. 22, 2011, 10 pages.

Wang et al., "Longitudinal chromatic aberration of the human infant eye", J. Opt. Soc. Am. A; Sep. 1, 2008; 25:9; p. 2263.

* cited by examiner

IOL WITH VARYING CORRECTION OF CHROMATIC ABERRATION

PRIORITY APPLICATION

This application claims priority to U.S. provisional application Ser. No. 61/185,510, filed on Jun. 9, 2009, the contents which are incorporated herein by reference.

RELATED APPLICATIONS

This application is related to co-pending application Ser. No. 12/780,244 entitled "ZONAL DIFFRACTIVE MULTIFOCAL INTRAOCULAR LENS WITH CENTRAL MONOFOCAL DIFFRACTIVE REGION" claiming priority to application Ser. No. 61/185,512 filed on the same day as the application to which the present application claims priority.

BACKGROUND

The present invention relates generally to ophthalmic lenses, and more particularly to intraocular lenses (IOLs) that provide compensation for chromatic aberrations.

Intraocular lenses are employed routinely to replace an occluded natural crystalline lens via cataract surgery. In other cases, an intraocular lens can be implanted in a patient's eye while retaining the natural crystalline lens to improve the patient's vision. Both monofocal and multifocal IOLs are known. While monofocal IOLs provide a single focusing power, multifocal IOLs can provide multiple focusing powers—typically two—to provide a degree of accommodation, commonly known as pseudo accommodation.

Many conventional IOLs, however, exhibit chromatic aberrations that can degrade their efficiency in concentrating the light energy incident thereon onto the patient's retina. Nor are such conventional IOLs typically designed to address the chromatic aberrations inherent in the lens and/or present in the optical system of the patient's eye.

Accordingly, there is an ongoing need for enhanced ophthalmic lenses, and particularly IOLs, with improved performance as compared to conventional IOLs.

SUMMARY

In a particular embodiment of the present invention, an ophthalmic lens includes an optical filter operable to filter out at least visible light having a wavelength less than 450 nm. The lens also includes a first diffractive structure adapted to produce a focus for visible light in a first wavelength range above 550 nm and to reduce longitudinal chromatic aberration to less than one diopter for incoming visible light in the first wavelength range. The lens also includes a second diffractive structure outside the first diffractive structure in a radial direction and adapted to produce a focus for visible light in a second wavelength range between 450 nm and 550 nm. The second diffractive structure is also adapted to reduce longitudinal chromatic aberration for incoming visible light in the second wavelength range to less than one diopter while allowing longitudinal chromatic aberration in the first wavelength range in an amount greater than the first diffractive structure.

In another embodiment, a method of manufacturing an IOL includes determining a first profile for a first diffractive structure adapted to produce a focus for visible light in a first wavelength range above 550 nm and to reduce longitudinal chromatic aberration to less than one diopter for incoming visible light in the first wavelength range. The method also includes determining a second profile for a second diffractive structure outside the first diffractive structure in a radial direction and adapted to produce a focus for visible light in a second wavelength range between 450 nm and 550 nm. The second diffractive structure also reduces longitudinal chromatic aberration for incoming visible light in the second wavelength range to less than one diopter while allowing longitudinal chromatic aberration in the first wavelength range in an amount greater than the first diffractive structure. The method then includes forming an ophthalmic lens with the first profile and the second profile and incorporating an optical filter operable to filter out at least visible light having a wavelength less than 450 nm.

In another embodiment, a method of manufacturing an IOL includes determining an optical filter operable to filter out at least light having a wavelength below 450 nm. The method also includes determining a first profile for at least one central diffractive structure having a radius within a selected pupil size for photopic conditions. The at least one diffractive structure is configured to correct longitudinal chromatic aberration to less than one diopter in a wavelength range corresponding to peak visual receptivity for photopic vision. The method further includes determining a second profile for an optical region outside the radius of the first diffractive structure. The optical region is configured to allow longitudinal chromatic aberration in an amount greater than the longitudinal chromatic aberration allowed by the at least one diffractive structure. The longitudinal chromatic aberration allowed by the optical region shifts light energy from a peak visual receptivity for photopic vision toward a peak visual receptivity for scotopic vision, and the longitudinal chromatic aberration allowed by the optical region is less than one diopter in a wavelength range corresponding to the peak visual receptivity for scotopic vision. The method then includes manufacturing the ophthalmic lens with the optical filter and the first and second profiles for the at least one central diffractive region and the optical region.

Further understanding of various aspects of the invention can be obtained by reference to the following detailed description in conjunction with the drawings, which are discussed briefly below.

DETAILED DESCRIPTION

The present invention generally provides for an intraocular lens with two diffractive structures with a common focus providing chromatic aberration for two different wavelength ranges used in conjunction with an optical filter to limit the spectrum of colors that require correction. A first diffractive structure provides chromatic aberration correction for relatively long wavelengths above 550 nm, while a second diffractive structure surrounding the first diffractive structure provides chromatic aberration correction within a shorter wavelength range while allowing chromatic aberration in the longer wavelength range. In operation, the combination of diffractive structures provides good correction for chromatic aberration in small pupil conditions. The outer diffractive element acts in large-pupil conditions to provide clear images free of chromatic aberration for shorter wavelengths, corresponding to the peak sensitivity of the eye in low-light conditions. The combination of diffractive elements, along with the restricted spectrum of the light, effectively manages chromatic aberration correction in different wavelength ranges to allow for clear vision under a variety of lighting conditions.

In the embodiments that follow, the salient features of various aspects of the invention are discussed in connection with intraocular lenses (IOLs). The teachings of the invention can also be applied to other ophthalmic lenses, such as contact lenses. The term "intraocular lens" and its abbreviation "IOL" are used herein interchangeably to describe lenses that are implanted into the interior of the eye to either replace the eye's natural lens or to otherwise augment vision regardless of whether or not the natural lens is removed. Intracorneal lenses and phakic intraocular lenses are examples of lenses that may be implanted into the eye without removal of the natural lens.

Figure 1B:
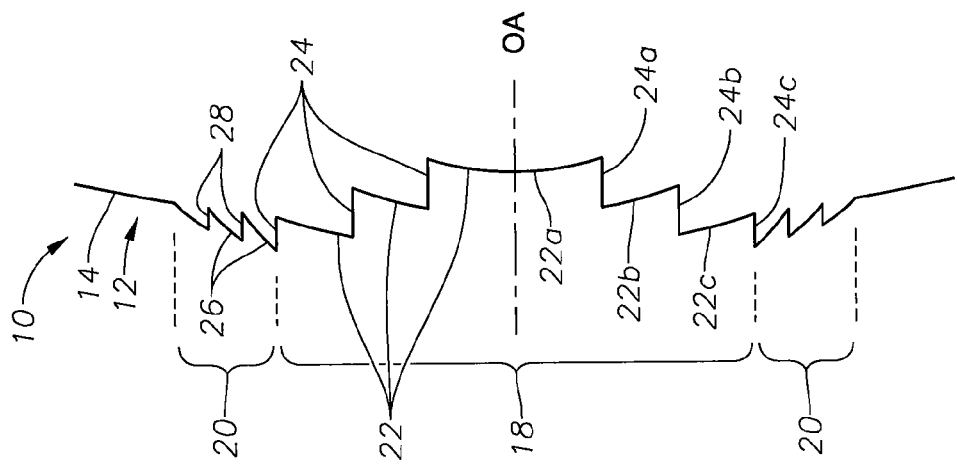
FIG. 1B shows a profile of the anterior surface of the IOL depicted in FIG. 1A from which the base profile of the anterior surface has been subtracted.
Figure 1A:
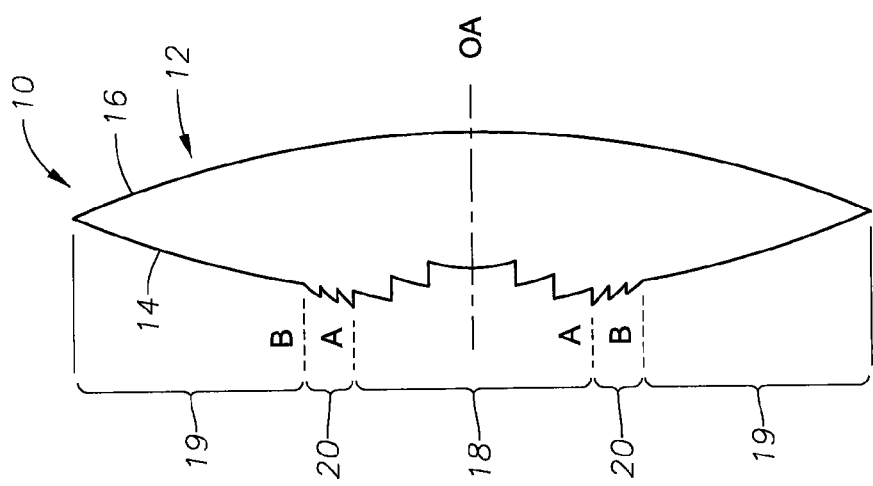
FIG. 1A is a schematic side view of an IOL in accordance with an embodiment of the invention.

FIGS. 1A and 1B schematically depict an intraocular lens (IOL) 10 in accordance with one embodiment of the invention that includes an optic 12 having an anterior surface 14 and a posterior surface 16 disposed about an optical axis OA. A first diffractive structure 18 is disposed on a central portion of the anterior surface, and is surrounded by a second diffractive structure 20, which extends from an outer boundary (A) of the monofocal structure 18 to an inner boundary (B) of an outer refractive region 19 of the anterior surface.

As shown in FIG. 1A, in this embodiment both the anterior surface 14 and the posterior surface 16 of the IOL 10 have generally convex base profiles. In this example, the curvatures of the base profiles of the anterior and posterior surfaces are such that the lens body contributes refractively to the IOL's far-focus optical power. Further, as noted above, an outer refractive region 19 of the anterior surface extends from the outer boundary of the second diffractive structure to the periphery of the lens, which may contribute refractively to a far-focus optical power for large pupil sizes, e.g., in low light conditions.

Alternatively, the curvatures of the anterior and the posterior surfaces can be selected such that the lens body would contribute refractively to the lens's near-focus optical power. In other cases, the anterior and posterior surfaces can have substantially flat profiles such that the near and far-focus optical power of the lens are due to the diffractive contributions from the first and second diffractive structures with no substantial (if any) refractive contribution from the lens body.

The optic can be formed of any suitable biocompatible material, including a plurality of biocompatible polymeric materials. Some examples of such materials include, without limitation, a soft acrylic material utilized for forming commercial lenses commonly known as Acrysof (a cross-linked copolymer of 2-phenylethyl acrylate and 2-phenylethyl methacrylate), silicone and hydrogel. Techniques according to the present invention may be particularly suitable for high refractive index materials over 1.5, which produce significant chromatic dispersion. Suitable optical filters may include materials that can be incorporated into a material proposed for the IOL 10 and may correspond to a range known to improve visual acuity and/or to protect retinal tissue from potentially harmful wavelengths, similar to a natural crystalline lens. A suitable material, for example, would be the Acrysof Natural chromophore as described in U.S. Pat. Nos. 5,470,932 and 5,543,504, both of which are incorporated herein by reference. Though not shown, the IOL 10 can also include a plurality of fixation members (e.g., haptics) that can facilitate its placement in a patient's eye.

An advantage of certain embodiments of the present invention is that a monofocal IOL may be made thinner than a similar monofocal IOL that is purely refractive on account of the improved visual acuity from chromatic aberration correction. To obtain similar performance, a purely refractive IOL must have better refractive performance, such as better correction for off-axis and peripheral rays, which ordinarily requires more refractive material. The chromatic aberration correction can improve visual acuity without requiring extensive modifications to the refractive properties of the IOL, which in turn requires less refractive material. This may advantageously be exploited to reduce a thickness of the IOL in order to permit a smaller incision. Moreover, it provides an advantage over methods using multiple materials, some having a lower refractive index, to correct chromatic aberration, which again increases the amount of lens material required.

Another advantage of IOLs of various embodiments of the present invention can be a relatively lower diffractive power. In previous lenses that attempted to uniformly correct chromatic aberration over an entirety of the lens for visible wavelengths, the diffractive power had to be sufficiently high to correct for aberrations even at a periphery of the lens, which in turn required a high power for the diffractive element. Also, as the nominal refractive power of the lens increases, the chromatic aberration becomes correspondingly greater, thus requiring more diffractive power. According to U.S. Pat. No. 4,655,565 to Freeman, a relatively low-power lens with a nominal power of 12 D would require 3.4 D of (negative) diffractive power to produce a net longitudinal chromatic aberration correction of 1 diopter. As the diffractive power required increases, the number of echelettes required also increases, creating a greater likelihood of visual disturbances, such as glare, produced by the diffractive structure.

By way of contrast with prior lenses, various embodiments of the present invention allow the diffractive power of both the first diffractive structure and the second diffractive structure to be less than what is expected from the teaching of U.S. Pat. No. 4,655,565, thus providing improved visual performance due to chromatic aberration correction without negative effects that might otherwise be produced by the correction. For example, longitudinal chromatic aberration could be reduced to less than a diopter within a central zone with a diffractive power of 2.39 for the first diffractive structure in a lens with nominal power of 6 D, a diffractive power of 3.58 with a nominal lens power of 21 D, and a diffractive power of 4.56 with a nominal lens power of 34 D. Likewise, the diffractive power of the second diffractive structure, which corrects chromatic aberration within a lower wavelength range, can be relatively low. For example, longitudinal chromatic aberration within a target range less than 550 nm could be reduced to less than one diopter for a diffractive power of 2.85 D with a nominal lens power of 6 D, a diffractive power of 3.58 with a nominal lens power of 4.22 D, and a diffractive power of 8.00 with a nominal lens power of 34 D.

With reference to FIG. 1B, the first diffractive structure 18 includes a plurality of diffractive echelettes 22 separated from one another by a plurality of step heights 24 such that the diffractive structure 18 diffracts light into one or more orders. In this example, the step heights 24 exhibit decreasing heights as a function of increasing distance from the center of the anterior surface (i.e., the intersection of the optical axis with the anterior surface). Suitable boundary conditions can be selected to provide a smooth transition between the first diffractive structure 18 and a first echelette 24c of a second diffractive structure. Further details regarding selection of the step heights in general can be found in U.S. Pat. No. 5,699,142 to Lee et al., which is herein incorporated by reference in its entirety and which in particular describes apodization of the diffractive pattern in a way that can reduce glare and/or other negative effects associated with light at the periphery of the lens. Further details regarding the diffractive correction of chromatic aberration may be found in U.S. Pat. No. 4,655,565 to Freeman and U.S. Pat. No. 5,117,306 to Cohen, both of which are incorporated herein by reference.

The first diffractive structure 18 of the IOL 10 exhibits a negative longitudinal chromatic aberration. That is, its optical power increases with increasing wavelength (its focal length decreases for longer wavelengths). In contrast, the refractive power provided by the IOL 10 as well as the human eye exhibit a positive chromatic aberration characterized by a decrease in optical power (increase in focal length) as a function of an increase in wavelength. Hence, the first diffractive structure can be adapted to compensate for the positive chromatic aberration of the human eye and that of the lens itself for far and/or near vision. The first diffractive structure 18 is adapted to provide correction for chromatic aberration for a wavelength range including wavelengths over 550 nm so as to provide minimal chromatic aberration over a relatively wide range of visible colors. The first diffractive structure 18 corresponds to a small pupil size typical of bright lighting conditions. In bright lighting conditions, there is significant sensory response by the visual receptors known as cone cells, which are sensitive to color variations. The visual receptivity of the eye under these conditions is referred to as "photopic" vision. In particular, the fovea of the human eye, which is responsible for high visual acuity, contains two types of cone cells with peak sensitivity above 550 nm. Thus, in terms of visual acuity, there can be a greater benefit by correcting chromatic aberration more stringently, which is to say, providing chromatic aberration correction for a longer wavelength range. The reduction of longitudinal chromatic aberration to less than a diopter over the wavelength ranges described herein is typically adequate to provide good visual acuity, so that value will be used herein as an indication of sufficient correction.

The second diffractive structure 20 also exhibits a negative chromatic aberration correction. The diffractive structures 18 and 20 differ, however, in that the chromatic aberration correction of the second diffractive structure 20 allows chromatic aberration to persist at the upper end of the wavelength range to a greater degree than the first diffractive structure 18. Thus, for example, the second diffractive structure 20 may correct chromatic aberration in a range of the filtered light from 450 nm to 550 nm. Because the second diffractive structure 20 is outside the first diffractive structure 18 in the radial direction, the correction in that region corresponds more closely to larger pupil conditions associated with low light. Under these conditions, there is typically insufficient light to trigger the cone cells, meaning that vision is dominated by the visual receptors known as rod cells having limited color sensitivity. The visual receptivity of the eye under these lighting conditions is known as "scotopic" vision. This means that the visual disturbance from chromatic aberration is less serious, particular for colors far from the peak sensitivity of the rod cells (around 498 nm). The chromatic aberration correction of the second diffractive structure 20 thus allows more effective transmission of light in the peak sensitivity area in low-light conditions, which is required for good visual acuity, while tolerating chromatic aberration for wavelengths that are less important under those conditions.

The described modifications may also be advantageously employed with other modifications pertaining to improved distance vision. For example, the diffractive structures 18 and 20 may be modified so that one focuses light to a near-vision or distant-vision focus in order to provide improved visual quality for that range. In low-light conditions where reading or other near-vision activities are unlikely to take place, more light energy can be directed to a distant focus by the second diffractive structure 20 in order to improve visual acuity in that range. Used in conjunction with chromatic aberration correction, the above IOL 10 can advantageously provide improved distance vision as well.

Figure 2:
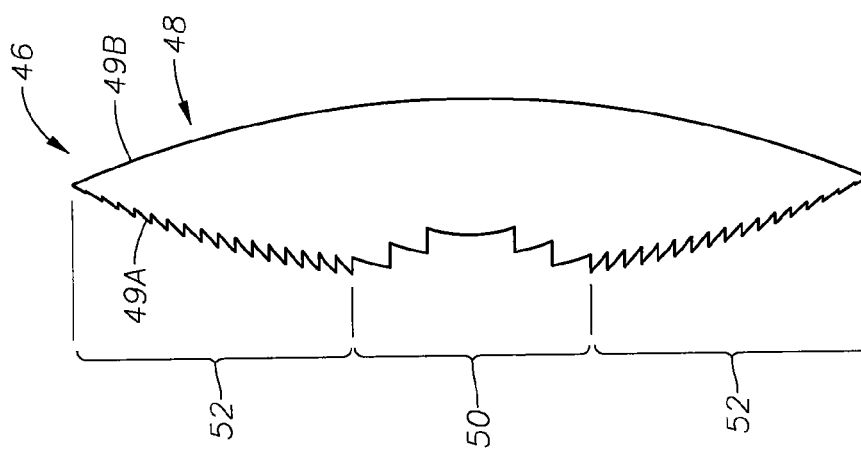
FIG. 2 is a schematic side view of an IOL having multiple diffractive structures extending to a periphery of the IOL according to another embodiment of the invention.

In the above embodiments the second diffractive structure 20 is truncated, that is, it does not extend to the periphery of the lens. In alternative embodiments, a first truncated diffractive structure 18 can be combined with an outer refractive structure allowing chromatic aberration to produce chromatic aberration correction in a central area of the IOL 10 while permitting chromatic aberration in an outer region of the lens. In other alternative embodiments, the second diffractive structure 20 can extend to the lens's periphery. By way of example, FIG. 2 schematically depicts such a lens 46 that includes an optic 48 having an anterior surface 49A and a posterior surface 49B. Similar to the previous embodiments, a first diffractive structure 50 is disposed on a central region of the anterior surface 49A, and is surrounded by a second diffractive structure 52 that extends from the outer boundary of the first diffractive structure to the periphery of the lens. The second diffractive structure 52 can include a plurality of diffractive echelettes that are separated from one another by a plurality of steps, which can have a substantially uniform or apodized heights, e.g., in a manner discussed above. In this case, the step associated with the second diffractive structure 52 exhibit decreasing heights as a function of increasing distance from the center of the anterior surface.

Figure 3:
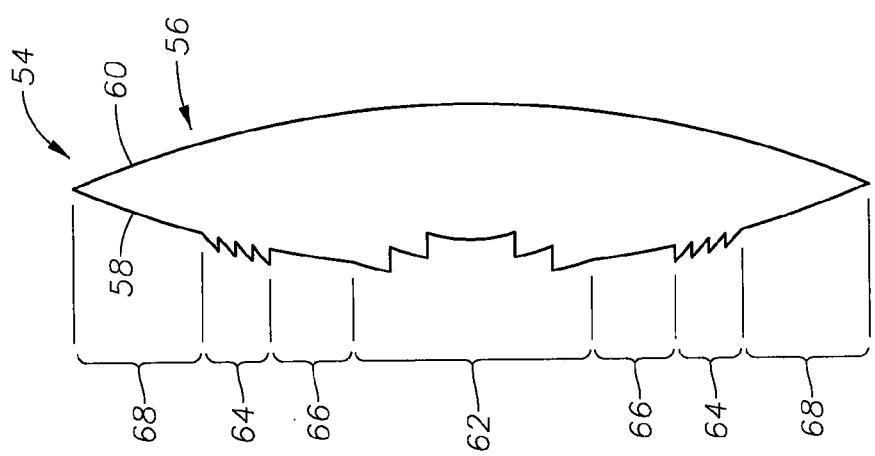
FIG. 3 is a schematic side view of an IOL having an annular refractive region separating first and second diffractive structures according to another embodiment of the invention.

FIG. 3 schematically depicts an IOL 54 according to another embodiment having an optic 56 with an anterior surface 58 and a posterior surface 60. A first diffractive structure 62 is disposed on a central portion of the anterior surface. The anterior surface further includes a second diffractive structure 64 that is separated from the first diffractive structure 62 by an annular refractive region 66. An outer refractive region 68 surrounds the bifocal structure.

Figure 4:
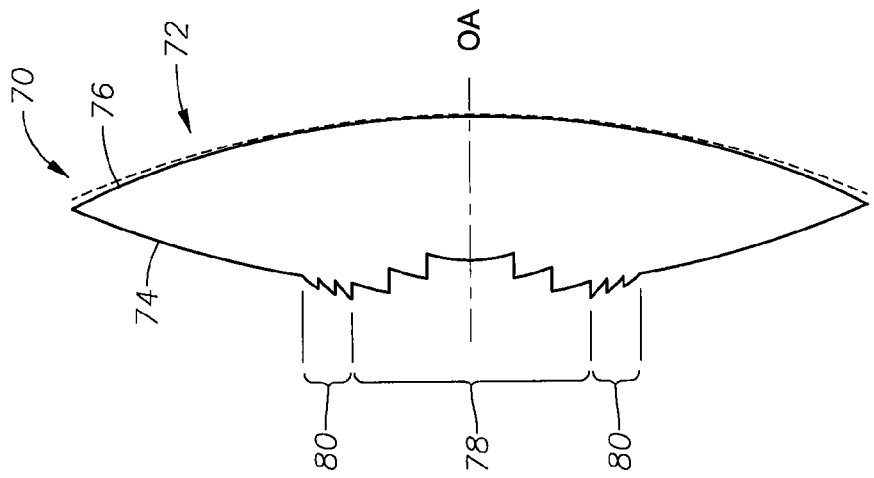
FIG. 4 is a schematic side view of an IOL in accordance with another embodiment of the invention in which the posterior surface of the lens exhibits an aspheric base profile for controlling spherical aberrations effect.

In some embodiments, a degree of asphericity can be imparted to the base profile of the anterior and/or the posterior surface of an IOL so as to ameliorate spherical aberrations effects. By way of example, FIG. 4 schematically depicts such an IOL 70 that includes an optic 72 having an anterior surface 74 and a posterior surface 76 disposed about an optical axis OA. Similar to the previous embodiments, a first diffractive structure 78 is disposed on a central region of the anterior surface 74 while a second diffractive structure 80 in the form of an annular region surrounds the first diffractive structure. The base profile of the posterior surface deviates from a putative spherical profile (shown by dashed lines), with the deviation progressively increasing as a function of increasing distance from the center of the posterior surface defined in this case as the intersection of the optical axis with the posterior surface. In some embodiments, the asphericity of the base profile of the posterior surface can be characterized by a conic constant. The asphericity can change spherical aberrations exhibited by the IOL and/or offset to some degree a predicted spherical aberration of a cornea. Although in this embodiment the base profile of the posterior surface is adapted to exhibit a degree of asphericity, in other embodiments, such an asphericity can be imparted to the anterior surface or both surfaces, and diffractive structures 18 and 20 may be superimposed on one or both surfaces. It is also possible to have a varying aspheric curvature on an aspheric surface, so that the aspheric profile may be defined by a first polynomial within a certain radius and a second polynomial outside that radius, which can also coincide with a radius of the first diffractive structure 18 and/or second diffractive structure 20 if desired. The base curve may also include higher-order asphericity.

Figure 5:
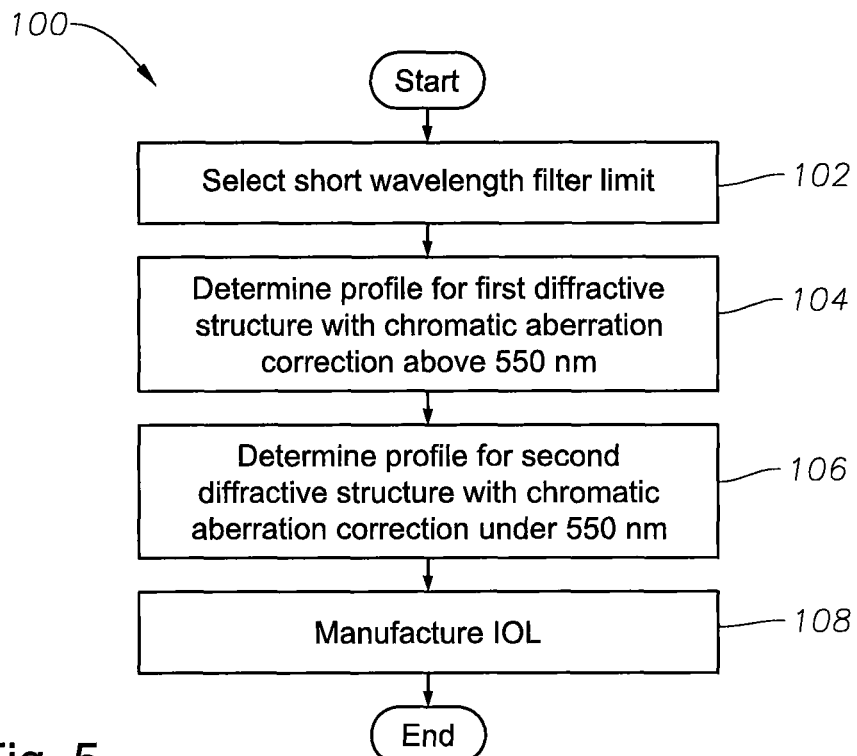
FIG. 5 is a flowchart illustrating a method of manufacturing an IOL according to a particular embodiment of the present invention.

FIG. 5 is a flowchart 100 depicting an example method of manufacturing an IOL according to particular embodiments of the present invention. At step 102, a limit for filtration of short wavelength light is determined. In a typical example, this limit may correspond to a known optical filter that can be incorporated into a material proposed for the IOL and may correspond to a range known to improve visual acuity and similar to a natural crystalline lens, such as, for example, filtering out light with a wavelength shorter than 450 nm. At step 104, a profile for a first diffractive structure providing chromatic aberration correction above 550 nm according to any of the various embodiments described herein, along with any suitable variations that would be apparent to one skilled in the art, is determined. In particular, the determination of the first diffractive profile can take into account desired power, suitable base curves for the anterior and/or posterior surfaces, asphericity or other aberration correction imparted to one or both surfaces, and the like.

At step 106, a profile for a second diffractive structure providing chromatic aberration correction for a range less than 550 nm while allowing chromatic aberration for wavelengths greater than 550 nm is determined, which may be according to any of the various embodiments described herein along with any suitable variations that would be apparent to one skilled in the art. In particular, the determination of the second diffractive profile can take into account desired power, suitable base curves for the anterior and/or posterior surfaces, asphericity or other aberration correction imparted to one or both surfaces, and the like. At step 108, an IOL with the first and second diffractive structures having the respective profiles determined in steps 104 and 106 along with an optical filter with the properties selected in step 102 is manufactured. Suitable manufacturing techniques may include any method of formation suitable to the materials, including but not limited to molding, ablating and/or lathing, along with any technique for providing an optical filter into the IOL, such as incorporation into the IOL material.

Figure 6:
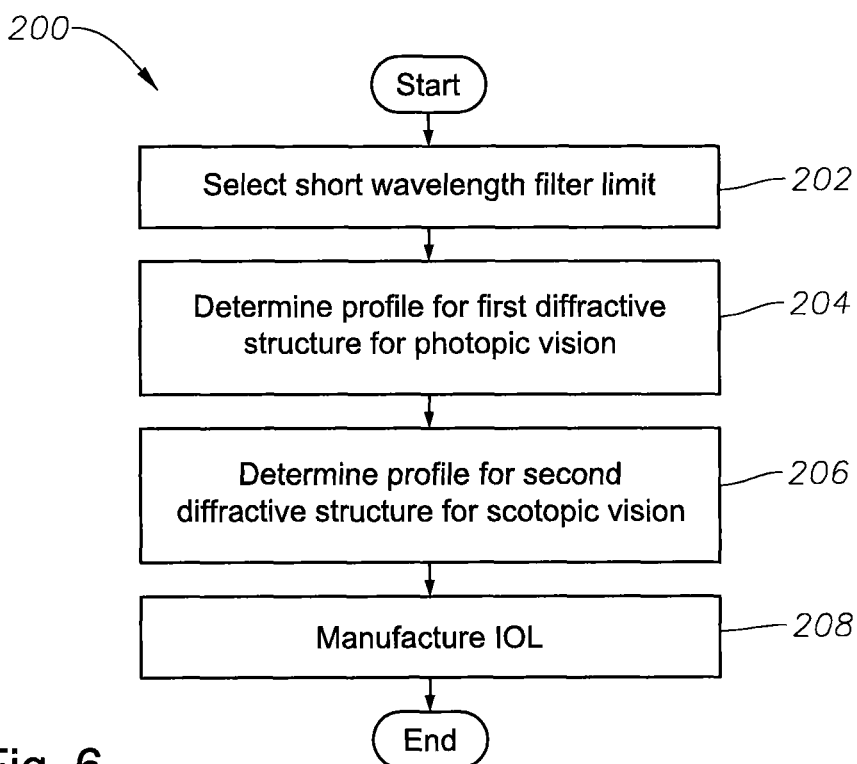
FIG. 6 is a flowchart illustrating another example method of manufacturing an IOL according to a particular embodiment of the present invention.

FIG. 6 is another flowchart 200 illustrating an example method of manufacturing an IOL according to a particular embodiment of the present invention. At step 202, a short wavelength limit for an optical filter of the IOL is determined. At step 204, a profile for a first diffractive structure is determined. The profile corrects chromatic aberration in order to maximize light intensity around a peak visual receptivity for photopic vision. At step 206, a profile for a second diffractive structure outside the first diffractive structure is determined. The profile corrects chromatic aberration in order to maximize light intensity near a peak visual receptivity for scotopic vision while allowing chromatic aberration in wavelengths far from peak sensitivity. At step 208, an IOL with the optical filter and the first and second diffractive structures is manufactured. Suitable manufacturing techniques may include any method of formation suitable to the materials, including but not limited to molding, ablating and/or lathing, along with any technique for providing an optical filter into the IOL, such as incorporation into the IOL material.

In a variation of the method shown in FIG. 6, the relative area covered by the first and second diffractive structures can be adjusted to shift the visible light energy as between the respective chromatic peaks of the diffractive structures. Such adjustments can allow more efficient transfer of light energy to the respective photopic and scotopic ranges. The adjustments may be analogous to the techniques for shifting light energy between foci described in U.S. Pat. Nos. 7,441,894 and 7,481,532 to Hong et al., both of which are incorporated herein by reference, but in this case, the energy shift is based on the relative light intensity as a function of wavelength.

In another embodiment, a similar effect can be produced by varying the boundary of the first diffractive structure 18 alone while allowing an outer region that is only refractive, replacing the determination of the profile for the second diffractive structure with determining a refractive profile outside the first diffractive structure. In such an embodiment, the first diffractive structure 18 still corrects for chromatic aberration in a central region of the IOL for a pupil size corresponding to photopic conditions, but the first diffractive structure 18 is truncated at a certain radius so that, in combination with the refractive power, the chromatic aberration from light entering the remainder of optic shifts light energy from a peak visual receptivity for photopic vision to a peak visual receptivity for scotopic vision. The human eye's response for wavelength in the peak sensitivity for scotopic vision tends to be slightly myopic, so the slight shift in power can help to focus light to increase the light intensity in the wavelength range of scotopic vision. Thus, chromatic aberration need not be corrected for the entire lens. Rather, the chromatic aberration correction needs only provide sufficient correction for photopic vision while allowing good scotopic vision in large-pupil conditions when the chromatic aberration of the overall optic is taken into account. For purposes of this specification, the range for peak visual sensitivity for photopic vision is 580 nm, plus or minus 30 nm, and the range for peak visual sensitivity for scotopic vision is 505 nm, plus or minus 30 nm.

Those having ordinary skill in the art will appreciate that various changes can be made to the above embodiments without departing from the scope of the invention. For example, rather than disposing both the first and the second diffractive structures on a single lens surface, one structure can be disposed on the lens's anterior surface and the other on its posterior surface. Additional diffractive structures beyond a first and second diffractive structure may also be included. Further, the base profiles of the anterior and posterior surfaces can be configured such that the lens body would contribute refractively to the IOL's near-focus optical power. Such variations and others apparent to one skilled in the art should be understood to fall within the scope of the invention as claimed.

The invention claimed is:

1. A monofocal ophthalmic lens having an optical power, comprising:
   An optical filter operable to filter out at least visible light having a wavelength less than 450 nm;
   a first monofocal diffractive structure adapted to produce a focus corresponding to the optical power for visible light in a first wavelength range above 550 nm and to reduce longitudinal chromatic aberration to less than one diopter for incoming visible light in the first wavelength range;

a second monofocal diffractive structure outside the first diffractive structure in a radial direction and adapted to produce a focus for visible light corresponding to the optical power in a second wavelength range between 450 nm and 550 nm and to reduce longitudinal chromatic aberration for incoming visible light in the second wavelength range to less than one diopter while allowing longitudinal chromatic aberration in the first wavelength range in an amount greater than the first diffractive structure.

2. The ophthalmic lens of claim 1, wherein a diffractive efficiency of the first diffractive structure is 100% for a design wavelength of 580 nm.

3. The ophthalmic lens of claim 1, wherein a diffractive efficiency of the second diffractive structure is 100% for a design wavelength of 505 nm.

4. The ophthalmic lens of claim 1, wherein the lens has an overall power up to 6 D and the first diffractive structure and the second diffractive structure each have a respective diffractive power less than 3 D.

5. The ophthalmic lens of claim 1, wherein the lens has an overall power up to 21 D and the first diffractive structure and the second diffractive structure each have a respective diffractive power less than 4.25 D.

6. The ophthalmic lens of claim 1, wherein the optical filter comprises a UV-absorbing material.

7. The ophthalmic lens of claim 1, wherein the ophthalmic lens is formed from a cross-linked copolymer of 2-phenylethyl acrylate and 2-phenylethyl methacrylate.

8. The ophthalmic lens of claim 1, wherein the focus of the first diffractive structure coincides with the focus of the second diffractive structure.

9. The ophthalmic lens of claim 1, wherein the focus of the second diffractive structure is a distance-vision focus.

10. The ophthalmic lens of claim 1, wherein the first diffractive structure extends to a radius of at least 2 mm, and the second diffractive structure extends to a radius of at least 3 mm.

11. A monofocal ophthalmic lens having an optical power, comprising:

an optical filter operable to filter out at least light having a wavelength below 450 nm;

at least one central monofocal diffractive structure having a radius within a selected pupil size for photopic conditions, wherein the at least one diffractive structure is configured to correct longitudinal chromatic aberration to less than one diopter in a wavelength range corresponding to peak visual receptivity for photopic vision; and a monofocal optical region outside the radius of the first diffractive structure having the optical power, the optical region configured to allow longitudinal chromatic aberration in an amount greater than the longitudinal chromatic aberration allowed by the at least one diffractive structure, wherein the longitudinal chromatic aberration allowed by the optical region shifts light energy from a peak visual receptivity for photopic vision toward a peak visual receptivity for scotopic vision and the longitudinal chromatic aberration allowed by the optical region is less than one diopter in a wavelength range corresponding to the peak visual receptivity for scotopic vision.

12. The ophthalmic lens of claim 11, wherein the optical region is a refractive region of the ophthalmic lens.

13. The ophthalmic lens of claim 11, wherein the optical region comprises a second diffractive structure allowing chromatic aberration to a greater degree than the at least one central diffractive structure in the wavelength range corresponding to the peak visual receptivity for photopic vision.

14. The ophthalmic lens of claim 13, wherein a relative area covered by the at least one central diffractive structure and the second diffractive structure at least partially produces the shift in light energy toward the peak visual receptivity for scotopic vision.

15. The ophthalmic lens of claim 13, wherein a refractive power of the optical region is adjusted to focus light to compensate for a myopic shift for scotopic vision.

* * * * *